US007578970B2

(12) United States Patent
Bowker

(10) Patent No.: US 7,578,970 B2
(45) Date of Patent: *Aug. 25, 2009

(54) METHODS OF INHIBITING GROWTH OF MICROORGANISMS USING DISINFECTANT COMPOSITIONS COMPRISING ORANGE OIL MIXTURES

(75) Inventor: Robert Bowker, Dover Plains, NY (US)

(73) Assignee: Knockout Technologies, Ltd., Scarsdale, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/056,642

(22) Filed: Mar. 27, 2008

(65) Prior Publication Data

US 2008/0187459 A1    Aug. 7, 2008

Related U.S. Application Data

(63) Continuation-in-part of application No. PCT/US2006/036978, filed on Sep. 22, 2006.

(60) Provisional application No. 60/720,811, filed on Sep. 27, 2005.

(51) Int. Cl.
*A61L 2/18* (2006.01)
*C11D 3/38* (2006.01)

(52) U.S. Cl. .................. 422/28; 510/463; 510/101; 510/111; 510/199; 510/302; 510/367; 510/372; 510/375; 510/384; 510/309

(58) Field of Classification Search .................. 422/28; 510/384, 101, 111, 199, 302, 309, 367, 372, 510/375, 463
See application file for complete search history.

(56) References Cited

U.S. PATENT DOCUMENTS 5,602,090 A     2/1997  Melikyan et al.
5,643,861 A     7/1997  de Guertechin et al.
5,863,663 A     1/1999  Mackey et al.
6,087,312 A     7/2000  Masotti et al.
6,114,298 A     9/2000  Petri et al.
6,316,399 B1   11/2001  Melikyan et al.
6,846,498 B2    1/2005  Death et al.
6,939,839 B2    9/2005  Johnson
7,439,218 B2 * 10/2008  Bowker ........................ 510/463
2004/0180804 A1 9/2004  Johnson

FOREIGN PATENT DOCUMENTS

EP      0842604 A1    5/1998

OTHER PUBLICATIONS

Declaration by Bruce Peterson; filed May 2, 2008 in U.S. Appl No. 11/525,507 (now U.S. Patent No. 7,439,218 B2).*
Vargas, et al. "Antimicrobial and Antioxidant Compounds in the Nonvolatile Fraction of Expressed Orange Essential Oil" Journal of Food Protection, vol. 62 No. 8, 1999, pp. 929-932.
Moshonas, et al. "Aldehydes, Ketones and Esters in Valencia Orange Peel Oil" Journal of Food and Science vol. 34, 1969.
Vora, et al. "Preparation of Chemical Composition of Orange Oil Concentrates" Journal of Food and Science, vol. 48, 1983.
Derwent Abstract of DE19523320 A1.
Coleman et al. "Composition of Orange Essence Oil" Journal of Food and Science vol. 34 No. 6 (1969), pp. 610-611.

* cited by examiner

*Primary Examiner*—Sean E Conley
(74) *Attorney, Agent, or Firm*—Nixon Peabody LLP

(57) ABSTRACT

The present invention discloses a highly potent, non-toxic, disinfectant that can be used for a wide breadth of applications. The disinfectant comprises hydrogen peroxide ($H_2O_2$), orange terpene oil, orange valencia oil, a non-ionic emulsifier (polysorbate 80), and water ($H_2O$). Applications of the disinfectant include, but are not limited to, uses as a mouthwash, skin cleanser, or as a germicidal for disinfecting surfaces such as foodstuff, plant matter, leather, wood, metal, plastic and fabrics. Methods for using the disinfectant composition of the invention are also provided.

11 Claims, 7 Drawing Sheets

SUMMARY OF CLINICAL OBSERVATIONS

TIME AFTER DOSING

| DAY | HOUR | MINUTES | NO. ALIVE | CLINICAL SIGNS |
|---|---|---|---|---|
| 0 | - | | 3 | #1 - 3: NO ABNORMALITIES |
| 0 | | 30 | 3 | #1 - 3: LETHARGIC |
| 0 | +1 | | 3 | #1 LETHARGIC, 2 AND 3 NORMAL |
| 0 | +2 | | 3 | #1 - 3: LETHARGIC, #1 WITH RED NASAL DISCHARGE |
| 0 | +4 | | 3 | #1 - 3 NORMAL |
| 1 | am | | 3 | #1 - 3 NORMAL |
| 1 | pm | | 3 | #1 - 3 NORMAL |
| 2 | | | 3 | #1 - 3 NORMAL |
| 3 | | | 3 | #1 - 3 NORMAL |
| 4 | | | 3 | #1 - 3 NORMAL |
| 5 | | | 3 | #1 - 3 NORMAL |
| 6 | | | 3 | #1 - 3 NORMAL |
| 7 | | | 3 | #1 - 3 NORMAL |
| 8 | | | 3 | #1 - 3 NORMAL |
| 9 | | | 3 | #1 - 3 NORMAL |
| 10 | | | 3 | #1 - 3 NORMAL |
| 11 | | | 3 | #1 - 3 NORMAL |
| 12 | | | 3 | #1 - 3 NORMAL |
| 13 | | | 3 | #1 - 3 NORMAL |
| 14 | | | 3 | #1 - 3 NORMAL |

*FIG. 1*

PRIMARY EYE IRRITATION SCORES

| ANIMAL NUMBER | SEX | Wt. (kg) | TIME AFTER DOSING (hrs) | OPACITY | | CORNEA PERCENT AREA | | IRIS | | CONJUCTIVAE REDNESS | | CHEMOSIS | | DISCHARGE | |
|---|---|---|---|---|---|---|---|---|---|---|---|---|---|---|---|
| | | | | L | R | L | R | L | R | L | R | L | R | L | R |
| 38370 | M | 2.4 | 1 Hr | 0 | 0 | 0 | 0 | 0 | 0 | 1 | 2 | 0 | 3 | 0 | 2 |
| | | | 24 Hrs | 0 | 0 | 0 | 0 | 0 | 1 | 1 | 2 | 0 | 2 | 0 | 2 |
| | | | 48 Hrs | 0 | 0 | 0 | 0 | 0 | 1 | 0 | 2 | 0 | 2 | 0 | 2 |
| | | | 72 Hrs | 0 | 0 | 0 | 0 | 0 | 0 | 0 | 1 | 0 | 1 | 0 | 1 |
| | | | 96 Hrs | 0 | 0 | 0 | 0 | 0 | 0 | 0 | 1 | 0 | 0 | 0 | 0 |
| | | | 7 DAYS | 0 | 0 | 0 | 0 | 0 | 0 | 0 | 0 | 0 | 0 | 0 | 0 |
| 38373 | M | 2.5 | 1 Hr | 0 | 0 | 0 | 0 | 0 | 0 | 0 | 2 | 0 | 2 | 0 | 1 |
| | | | 24 Hrs | 0 | 0 | 0 | 0 | 0 | 1 | 0 | 2 | 0 | 2 | 0 | 2 |
| | | | 48 Hrs | 0 | 0 | 0 | 0 | 0 | 1 | 0 | 2 | 0 | 2 | 0 | 2 |
| | | | 72 Hrs | 0 | 0 | 0 | 0 | 0 | 0 | 1 | 2 | 0 | 1 | 0 | 1 |
| | | | 96 Hrs | 0 | 0 | 0 | 0 | 0 | 0 | 0 | 1 | 0 | 0 | 0 | 0 |
| | | | 7 DAYS | 0 | 0 | 0 | 0 | 0 | 0 | 0 | 0 | 0 | 0 | 0 | 0 |
| 38375 | M | 2.4 | 1 Hr | 0 | 0 | 0 | 0 | 0 | 0 | 0 | 2 | 0 | 2 | 0 | 1 |
| | | | 24 Hrs | 0 | 0 | 0 | 0 | 0 | 1 | 0 | 2 | 0 | 2 | 0 | 2 |
| | | | 48 Hrs | 0 | 0 | 0 | 0 | 0 | 1 | 0 | 2 | 0 | 2 | 0 | 1 |
| | | | 72 Hrs | 0 | 0 | 0 | 0 | 0 | 0 | 0 | 2 | 0 | 1 | 0 | 1 |
| | | | 96 Hrs | 0 | 0 | 0 | 0 | 0 | 0 | 0 | 1 | 0 | 0 | 0 | 0 |
| | | | 7 DAYS | 0 | 0 | 0 | 0 | 0 | 0 | 0 | 0 | 0 | 0 | 0 | 0 |

*FIG. 2*

SCALE FOR SCORING OCULAR LESIONS

| OBSERVATION | VALUE |
|---|---|
| CORNEA | |
| (A) OPACITY - DEGREE OF DENSITY (AREA MOST DENSE TAKEN FOR READING) | |
| NO ULCERATION OR OPACITY | 0 |
| SCATTERED OR DIFFUSE AREAS, DETAILS OF IRIS CLEARLY VISIBLE | 1* |
| EASILY DISCERNIBLE TRANSLUCENT AREAS, DETAILS OF IRIS SLIGHTLY OBSCURED | 2* |
| NACROUS AREA, NO DETAILS OF IRIS VISIBLE, SIZE OF PUPIL BARELY DISCERNIBLE | 3* |
| OPAQUE, IRIS NOT DISCERNIBLE THROUGH OPACITY | 4* |
| (B) AREA OF CORNEA INVOLVED | |
| ONE QUARTER (OR LESS) BUT NO ZERO | 1 |
| GREATER THAN ONE QUARTER, BUT NOT LESS THAN HALF | 2 |
| GREATER THAN ONE HALF, BUT LESS THAN THREE QUARTERS | 3 |
| GREATER THAN THREE QUARTERS, UP TO WHOLE AREA | 4 |
| IRIS | |
| (A) <u>VALUES</u> | |
| NORMAL | 0 |
| MARKEDLY DEEPENED RUGAE, CONGESTION, SWELLING, MODERATE | 1* |
| CIRCUMCORNEAL HYPEREMIA, | 2* |
| OR INJECTION (ANY OF THESE OR COMBINATION OF ANY THEREOF); | |
| IRIS STILL REACTING TO LIGHT (SLUGGISH REACTION IS POSITIVE) | |
| NO REACTION TO LIGHT, HEMORRHAGE, GROSS DESTRUCTION (ANY OR ALL OF THESE) | |
| SCORE EQUALS (A) x 5 | TOTAL MAXIMUM = 10 |
| CONJUCTIVAE | |
| (A) REDNESS - REFERS TO PALPEBRAL AND BULBAR CONJUCTIVAE, CORNEA AND IRIS | |
| BLOOD VESSELS NORMAL | 0 |
| SOME BLOOD VESSELS DEFINITELY HYPEREMIC (INJECTED) | 1 |
| DIFFUSE, CRIMSON COLOR, INDIVIDUAL VESSELS NOT EASILY DISCERNIBLE | 2* |
| DIFFUSE BEEFY RED | 3* |

*FIG. 3*

EVALUATION OF SKIN REACTIONS

| ERYTHEMA AND ESCHAR FORMULATION | SCORE |
| --- | --- |
| NO ERYTHEMA | 0 |
| VERY SLIGHT ERYTHEMA (BARELY PERCEPTIBLE) | 1 |
| WELL-DEFINED ERYTHEMA | 2 |
| MODERATE TO SEVERE ERYTHEMA | 3 |
| SEVERE ERYTHEMA (BEET-REDNESS) TO SLIGHT ESCHAR FORMULATION (INJURIES IN DEPTH) | 4 |

| EDEMA FORMULATION | SCORE |
| --- | --- |
| NO EDEMA | 0 |
| VERY SLIGHT EDEMA (BARELY PERCEPTIBLE) | 1 |
| SLIGHT EDEMA (EDGES OF AREA WELL DEFINED BY DEFINITE RAISING) | 2 |
| MODERATE EDEMA (RAISED APPROXIMATELY 1 mm) | 3 |
| SEVERE EDEMA (RAISED MORE THAN 1 mm AND EXTENDING BEYOND AREA OF EXPOSURE) | 4 |

*FIG. 4*

INDIVIDUAL PRIMARY IRRITATION SCORES

| RABBIT NUMBER | TIME AFTER SCORING | | | | | | | |
|---|---|---|---|---|---|---|---|---|
| | 30 - 60 MINUTES | | 24 HOURS | | 48 HOURS | | 72 HOURS | |
| | ERYTHEMA | EDEMA | ERYTHEMA | EDEMA | ERYTHEMA | EDEMA | ERYTHEMA | EDEMA |
| 38397 | 1 | 0 | 0 | 0 | 0 | 0 | 0 | 0 |
| 38390 | 1 | 0 | 0 | 0 | 0 | 0 | 0 | 0 |
| 38383 | 1 | 0 | 1 | 0 | 1 | 0 | 0 | 0 |

*FIG. 5*

TEST RESULTS

| DILUTION | AVIAN INFLUENZA A VIRUS TITER | |
| --- | --- | --- |
| | Lot No. 14-G-07 | Lot No. 14-G-03 |
| $10^{-2}$ | — — — — | — — — — |
| $10^{-3}$ | — — — — | — — — — |
| $10^{-4}$ | — — — — | — — — — |
| $10^{-5}$ | — — — — | — — — — |
| $10^{-6}$ | — — — — | — — — — |
| $10^{-7}$ | — — — — | — — — — |
| (ELD/EID$_{50}$/mL) | $\leq 10^{1.50}$ | $\leq 10^{1.50}$ |

KEY: — = AVIAN INFLUENZA A VIRUS WAS NOT DETECTED, NO HEMAGGLUTINATION OBSERVED

*FIG. 6*

NEUTRALIZER EFFECTIVENESS AND TOXICITY RELATED CONTROLS
Lot No. 14-G-03

| DILUTION | TOXICITY CONTROL | TOXICITY-RELATED VIRAL INTERFERENCE CONTROL | NEUTRALIZER EFFECTIVENESS CONTROL |
|---|---|---|---|
| $10^{-2}$ | 0000 | ++++ | ++++ |
| $10^{-3}$ | 0000 | ++++ | ++++ |
| $10^{-4}$ | 0000 | ++++ | ++++ |

*FIG. 7A*

CONTROL RESULTS

| DILUTION | AVIAN INFLUENZA A VIRUS TITER | | |
|---|---|---|---|
| | PLATE RECOVERY CONTROL | COLUMN TITER CONTROL | VIRUS STOCK TITER |
| $10^{-1}$ | PNS | PNS | ++++ |
| $10^{-2}$ | ++++ | ++++ | ++++ |
| $10^{-3}$ | ++++ | ++++ | ++++ |
| $10^{-4}$ | ++++ | ++++ | ++++ |
| $10^{-5}$ | ++++ | ++++ | ++++ |
| $10^{-6}$ | ++−− | −+++ | +−++ |
| $10^{-7}$ | −−−+ | +−−+ | +−++ |
| $10^{-8}$ | ND | ND | −−−− |
| ($ELD/EID_{50}/mL$) | $\geq 10^{6.23}$ | $\geq 10^{6.50}$ | $10^{7.17}$ |

*FIG. 7B*

CONTROL RESULTS

| HOST VIABILITY CONTROL |
|---|
| −−−− |

*FIG. 7C*

METHODS OF INHIBITING GROWTH OF MICROORGANISMS USING DISINFECTANT COMPOSITIONS COMPRISING ORANGE OIL MIXTURES

CROSS REFERENCE TO RELATED APPLICATIONS

This application is a Continuation-in-part Application of International Application PCT/US2006/036978 filed on Sep. 22, 2006, which claims the benefit under 35 U.S.C §119(e) of U.S. Provisional Application No. 60/720,811 filed Sep. 27, 2005.

FIELD OF INVENTION

The present invention relates generally to an environmentally friendly, non-toxic, food grade, disinfectant composition that can be used for multiple applications including, but not limited to, uses as a mouthwash, skin cleanser, or as a germicidal for disinfecting surfaces such as foodstuff, plant matter, leather, wood, metal, plastic and fabrics.

BACKGROUND OF THE INVENTION

A number of products have been developed for the purpose of disinfecting and cleaning. However, many of these products use toxic, poisonous chemicals that are detrimental to the environment and to our health.

Hydrogen peroxide is a strong, environmentally friendly, disinfectant with a broad spectrum of antimicrobial activity that has been widely used in the healthcare field. Unfortunately, hydrogen peroxide is also a strong oxidizing agent that in high concentrations can damage tissue and damage surfaces such as foodstuff, making them more vulnerable to pathogenic penetration.

Essential oils, are natural products known to have antimicrobial properties and disinfectant solutions based on essential oils have been formulated, U.S. Pat. No. 6,846,498. However, the potency and spectrum of action of many of these formulations lag behind those exhibited by other antimicrobials. Furthermore, formulations are difficult to make because the oils are not readily miscible in water.

SUMMARY OF INVENTION

The present invention is directed to disinfectant compositions and their use.

The invention provides a disinfectant composition comprising hydrogen peroxide ($H_2O_2$), orange terpene oil, orange valencia oil, a non-ionic emulsifier (e.g. polysorbate 80), and deionized or distilled water ($H_2O$). The composition can include varied amounts of each of these ingredients.

In one embodiment, the orange terpene oil is present in the composition from 5% to 40% v/v, the orange valencia oil is present in the composition from 5% to 40% v/v, the non-ionic emulsifier is present in the composition from 5% to 50% v/v, the distilled or deionized $H_2O$ is present in the composition from 5% to 80% v/v and the hydrogen peroxide is present in the composition from 1.5% to 8% $H_2O_2$ w/v. In another embodiment, the composition comprises one half as much non-ionic emulsifier (e.g. polysorbate) by volume as the combined volume of orange valencia oil and orange terpene oil.

In one preferred embodiment the disinfectant composition comprises 5.25% $H_2O_2$ (15% of a 35% hydrogen peroxide solution), 10% v/v orange terpene oil, 5% v/v orange valencia oil, 10% v/v polysorbate 80, and 60% v/v distilled water.

In one embodiment, the disinfectant composition further comprises an antioxidant preservative of $H_2O_2$ such as oil of rosemary.

In one embodiment, the composition further comprises antimicrobials such as quaternary ammonium compounds, triclosan, cetyl pyridium chloride, domiphen bromide, zinc compounds, sanguinanine soluble pyrophosphates, fluorides, alexidine, octonidine, and EDTA. In addition, the disinfectant composition can also comprise surfactants, common builders that improve surfactant effectiveness, saponifiers, chelating agents, and/or other solvents.

The invention provides a method for disinfecting surfaces comprising applying the composition to the surface.

The invention further provides a method for reducing the number of mold spores on a surface. The method comprises contacting the surface containing the mold spores with the composition.

BRIEF DESCRIPTION OF FIGURES

FIG. 1 shows a chart summarizing the results of an EPA acute oral toxicity test where three female Sprague-Dawley rats received an oral limit dose of 50000 mg/kg of a germicidal spray comprising 60% distilled water, 10% polysorbate 80, 5% orange valencia oil, 10% orange terpene oil, and 15% of a 35% hydrogen peroxide solution. Time after dosing, mortality and clinical signs are indicated.

FIG. 2 shows a chart summarizing the results of an EPA primary eye irritation test where the eyes of six New Zeland Rabbits were exposed to a germicidal spray comprising 60% distilled water, 10% polysorbate 80, 5% orange valencia oil, 10% orange terpene oil, and 15% of a 35% hydrogen peroxide solution. Various times after dosing, the L (left) and R (right) eye were given a score as indicated in FIG. 3.

FIG. 3 shows a chart referencing the scale used for scoring ocular lesions that are scored in the primary eye irritation test described herein.

FIG. 4 shows a chart referencing the scale used for scoring skin reactions in the primary dermal irritation test described herein.

FIG. 5 shows a chart summarizing the results of a EPA primary dermal irritation test where the skin of three New Zeland Rabbits were exposed to a germicidal spray comprising 60% distilled water, 10% polysorbate 80, 5% orange valencia oil, 10% orange terpene oil, and 15% of a 35% hydrogen peroxide solution. Effects of exposure were given a score as indicated in FIG. 4.

FIG. 6 shows a chart of the results of a Virucidal Efficacy Test indicating the measured titer of Avian Influenza Virus after exposure to a germicidal spray comprising 60% distilled water, 10% polysorbate 80, 5% orange valencia oil, 10% orange terpene oil, and 15% of a 35% hydrogen peroxide solution; lot 14-G-07 and lot 14-G-03, as described in Example V. (----) lines indicate that to virus was detected.

FIGS. 7A-7C show charts of the results of control experiments performed in the Virucidal Efficacy Test described in Example V. FIG. 7A shows the results of neutralizer effectiveness and toxicity related controls. FIG. 7B shows the plate recovery control, column titer control and virus stock titer control. FIG. 7C shows control results for the host viability control. For FIGS. 7A-7C; (0)=no toxicity observed. (+)=Avian Influenza A virus was detected, hemagglutination observed, (−)=Avian Influenza A virus was not detected, No hemagglutination observed, PNS=Post neutralized sample, ND=Not determined.

DETAILED DESCRIPTION

We have discovered a highly potent non-toxic, environmentally friendly, disinfectant that can be used for a wide breadth of applications. The disinfectant described herein is composed of food grade material and comprises hydrogen peroxide ($H_2O_2$), orange terpene oil, orange valencia oil, a non-ionic emulsifier (e.g. polysorbate 80), and distilled or deionized water ($H_2O$). The disinfectant is very potent and, as shown in Example 1, highly effective at killing microorganisms including, but not limited to, bacteria (gram positive or gram negative), bacterial spores, molds, fungi and viruses such as *Salmonella cholerasuis, Staphylococcus aureaus, Pseudomonas aeruginosa, Escherichia coli, Streptococcus pneumonia*, and *Listeria monocytogenes*, and Influenza virus.

An advantage of the disinfectant composition of the invention over other disinfectants is that it can be composed of entirely food grade materials while maintaining its high degree of potency against bacteria and other microorganisms. The non-toxic components of the composition described herein work synergistically against microorganisms. Not to be bound by theory, it is believed that the orange valencia oil together with the other components weakens the microorganisms (bacteria/fungus/mold spores/viruses) making them more vulnerable to the $H_2O_2$.

In one embodiment, the disinfectant composition further comprises oil of rosemary, e.g. CAS Number 8000-25-7, which can be obtained from Polarome International, Inc. (200 Theodore Conrad Drive, Jersey City, N.J. 07035).

Any non-ionic emulsifier can be used in the disinfectant composition of the invention, including, but not limited to, alkyl polyethyleneoxy ethers, alkyl phenol polyethyleneoxy ethers, polyethyleneoxy amines, polyethyleneoxy fatty acids, and alkyl dimethyl amino oxides. In another embodiment, the composition comprising hydrogen peroxide ($H_2O_2$), orange terpene oil, orange valencia oil, a non-ionic emulsifier, and distilled or deionized water ($H_2O$) does not comprise an anionic surfactant or an amphoteric surfactant.

In one embodiment, the non-ionic emulsifier of the disinfectant composition is polysorbate 80 (CAS Number 9005-65-6).

In one embodiment, the disinfectant is a composition that comprises 60% v/v distilled water, 10% v/v polysorbate 80, 5% v/v orange valencia oil, 10% v/v orange terpene oil, and 15% v/v of a 35% wt. % hydrogen peroxide solution (equivalent to 5.35% of $H_2O_2$). The composition can be used at full strength or can be diluted with water. Dilutions can range from 1:1 to 1:10,000.

The disinfectant composition can be formulated, if desired, as a gel, spray, foam, or paste, or as a disinfecting wipe, using standard formulations known in the art as appropriate.

The disinfectant composition can be made by mixing the components together using any known means. Preferably the components are mixed together sequentially. For example, the components are added in sequence to distilled water in the following order: orange terpene oil, orange valencia, then polysorbate 80. While being mixed at moderate speed, hydrogen peroxide is then added and mixed for approximately five minutes. In one preferred embodiment, the distilled water is kept between 90° and 100° Fahrenheit to facilitate the emulsification process.

The components can be obtained from any source. Preferably food grade components are used. As an example source, the orange terpene oil and orange valencia oil can be obtained from Polarome International, Inc. (200 Theodore Conrad Drive, Jersey City, N.J. 07035) (Orange Terpenes, CAS Number 68647-72-3, EINECS Number 232-433-8; Orange Oil Valencias, CAS Number 8008-57-9, EINECS Number 232-433-8) or from Ungerer & Company (4 Bridgewater Lane, Lincoln park N.J. 07035)); the polysorbate 80 can be obtained from Spectrum Chemicals (14422 South San Pedro Street, Gardena, Calif. 90248) and the hydrogen peroxide from Solvay Chemicals Inc. (1632 Haden Road, Houston Tex. 77015) or from FMC corporation (1735 Market Street Philadelphia, Pa. 19103), (Durox®35%). The orange valencia oil can be derived from a cold press expression method which preserves viable anti-oxidants. In one embodiment, the orange valencia oil has at least 1.4% aldehydes.

As used herein, the orange valencia oil (CAS-No. 8008-57-9 and CAS-No. 8028-48-6; EINECS Number 232-433-8; FEMA No., 2825, Tarrif No. 3301.12; FDA 182.2) is a cold pressed valencia type oil having about 00.1% Citral (CAS-No. 5392-40-5), about 0.4% Linalool (CAS-No. 78-70-6), about 0.3% Decanal, and a maximum of about 95% Limonene (CAS-No. 5989-27-5). Orange Valencia oil is a cold pressed oil obtained by expression from peels of partially ripened fruits. The color is a clear orange-yellow liquid (intensely yellow, orange or deep orange). The odor is of fresh sweet orange peel. Physical and chemical properties include a flash point of about 45° C., vapor pressure at 20° C. of about 1 hPa; and a density at 20° C. of about 0.84 g/cm$^3$; solubility in water about 0 g/L; optical rotation of about +94°-+99°. In one embodiment, the orange valencial oil is the product "Orange Oil Brazil Valencia Type" from Polarome International, Inc. (200 Theodore Conrad Drive, Jersey City, N.J. 07035) Article no. 40760. In one embodiment, the orange valencia oil is the product "Oil Orange Valencia" from Ungerer & Company (4 Bridgewater Lane, Lincoln park N.J. 07035). In one embodiment, the orange valencia oil by gas chromatograph contains the following components in approximated percent: Alpha Pinene 0.49%; Sabinene 0.33%; Myrcene 2.08%; Limonene 95.00%; Octanol 0.04%; Linalool 0.53%; Decanal 0.32%; Citral 0.20%; Undeacanal 0.03%; Dodecanal 0.07%; Valencene 0.07%; and Beta-sinensal 0.03%.

As used herein, the orange terpene oil is produced by a folding process (CAS-No. 68647-72-3 and CAS-No. 8008-57-9; EINECS Number 232-433-8, FDA 21 CFR 182.20, FEMA No. 2633; 2825; having about 96% Limonene (CAS-No. 5989-27-5), about 0.03% Linalool, and about 0.02% Decanal. The orange terpene oil is a clear colorless pale yellow liquid with a characteristic lemon-like odor. Physical and chemical properties include a boiling point of about 160-250° C., a flash point of about 50° C. (122° F.), vapor pressure at 20° C. of about 1.2 hPa; and a density at 20° C. of about 0.85 g/cm$^3$, solubility in water about 0.03 g/L; an optical rotation of about +96°-+105°. In one embodiment, the orange terpene oil is the product "Orange Terpenes" from Polarome International, Inc. (200 Theodore Conrad Drive, Jersey City, N.J. 07035) Article no. 41100. In one embodiment, the orange terpene oil is the product "Orange Terpenes" from Ungerer & Company (4 Bridgewater Lane, Lincoln park N.J. 07035). In one embodiment, the orange terpene oil by gas chromatograph contains the following components in approximated percent: Alpha Pinene 0.60%; Sabinene 0.32%; Myrcene 2.40%; Limonene 96.30%; Octanol 0.03%; Linalool 0.03%; Decanal 0.02%; Citral 0.02%; Undeacanal 0.00%; Dodecanal 0.00%; Valencene 0.00%; and Beta-sinensal 0.00%.

While it is preferable to use only food grade components in the composition, other non-food grade components can also be added.

The composition described herein can include multiple surfactants, including, but not limited to nonionic surfactants such as nonylphenol ethoxylate, alcohol ethoxylates, octylphenol ethoxylate, coconut diethanolamide (cocoamide DEA), unspecified nonionic surfactant; anionic surfactants such as linear alkylbenzene sulfonate (dodecylbenzene sulfonate), alcohol sulfates (lauryl sulfates), alcohol ether sulfates (lauryl ether sulfates, laureth sulfates), sodium alkyl polyether sulfonate, alkyl polyglycosides, unspecified anionic surfactant, and soap; amphoteric surfactants such as, alkylbetaine, unspecified amphoteric surfactant; and cationic surfactants such as alkyl dimethyl benzyl ammonium chlorides, unspecified quaternary ammonium chlorides or compounds, alkylaryl dimethyl ammonium chloride, dimethyl ethyl benzyl ammonium chloride, ethylbenzene ammonium chloride, didecyl dimethyl ammonium chloride, octyl dimethyl ammonium chloride.

The composition of the invention can further comprise common builders that improve surfactant effectiveness, saponifiers, chelating agents, and/or other solvents, examples of such additives include, but are not limited to, acetic acid, hydrochloric acid, citric acid, sodium hydroxide, potassium hydroxide, carbonates sodium carbonate, sodium bicarbonate, pyrophosphates, polyphosphates, phosphate esters, orthophosphates, sodium metasilicate, sodium silicate, ethanolamines, carbonates, silicates, EDTA, STPP, and zeolites/PCA, isopropanol, methanol, ethanol, 2-butoxyethanol, diethylene glycol ethyl ether, diethylene glycol, monomethylether, 1-methoxy-2-propanol, 2-2-butoxyethyoxyethanol, d-limonene, pine oil, tall oil, ammonia (ammonium hydroxide), hydrocarbons, propylene glycol, ethylene glycol, or 1,3-proponediol.

Although not necessary, it is possible to employ other antimicrobial agents in the composition of this invention, for example quaternary ammonium compounds, phenols, alcohols, sodium hypochlorite, pine oil or other known antimicrobial oils. Examples of quaternary ammonium compounds include, but are not limited to alkyl dimethyl benzyl ammonium chlorides, unspecified quaternary ammonium chlorides or compounds, alkylaryl dimethyl ammonium chloride, dimethyl ethyl benzyl ammonium chloride, ethylbenzene ammonium chloride, didecyl dimethyl ammonium chloride, and octyl dimethyl ammonium chloride. Preferably the quaternary ammonium compound is present in the composition at 0.01-1%. Example phenols include, but are not limited to ortho-benzyl parachlorophenol, ortho-phenylphenol, and para-tertiary-amylphenol. Preferably the phenol is present in the composition at 2-5%. Example alcohols include but are not limited to Isopropyl alcohol and ethanol. Preferably, sodium hypochlorite is present in the composition from 0.5-5%. Other exemplary antimicrobial agents include, but are not limited to, triclosan, cetyl pyridium chloride, domiphen bromide, zinc compounds, sanguinanine soluble pyrophosphates, fluorides, alexidine, octonidine, EDTA, and the like.

The non-toxic nature of the disinfectant described herein allows for its use not only in applications where the harshness of the disinfectant is irrelevant, but also in applications more sensitive in nature, for example when disinfecting skin, treating plants and food stuff, and killing oral microorganisms.

In one embodiment, the disinfectant described herein is used to sanitize porous or non-porous surfaces. Any surface can be cleaned using the disinfectant of the invention including, but not limited to, leather, wood, metal, plastic, synthetics, and fabrics.

The composition of the invention can disinfect surfaces containing bacteria, bacterial spores fungus, and/or viruses (DNA or RNA viruses).

The compositions can be used to inactivate vegetative bacteria and bacterial spores upon contact. Bacteria that can be inactivated by the compositions can be gram negative or gram positive bacteria. gram negative bacteria include, for example and without limitation, *Vibrio, Salmonella, Shigella, pseudomonas, Escherichia, Klebsiella, Proteus, Enterobacter, Serratia, Moraxella, Legionella, Bordetella, Gardnerella, Haemophilus, Neisseria, Brucella, Yersinia, Pasteurella, Bacteroids*, and *Helicobacter*. gram positive bacteria include, for example, and without limitation, *Bacillus, Clostridium, Arthrobacter, Micrococcus, Staphylococcus* (e.g. methicillin resistant *Staphylococcus aureus*, MRSA), *Streptococcus, Listeria, Corynebacteria, Planococcus, Mycobacterium, Nocardia, Rhodococcus, Andacidfast bacilli* such as *Mycobacterium*. In one embodiment the compositions can be used to inactivate *bacillus*, including, without limitation *B. anthracis, B. cereus, B. circulans, B. subtilis*, and *B. megaterium*. Compositions of the invention can also be used to inactivate *Clostridium*, e.g., *C. botulinum, C. perfringens*, and *C. tetani*. Other bacteria that can be inactivated by the composition include, but are not limited to, *H. influenzae, N. gonorrhoeae, S. agalactiae, S. pneumonia, S. pyogenes* and *V. cholerae*.

Contacting a virus with the composition of the invention can inactivate a virus.

The effect of compositions on viral agents can be monitored using any suitable means, such as, for example, plaque reduction assay (PRA), cellular enzyme-linked immunosorbent assay (ELISA), P-galactosidase assay, and electron microscopy (EM). Viruses which can be inactivated by contact with the composition include, without limitation, virus of the families Baculoviridae, Herpesviridae, Iridoviridae, Poxyiridae, "African Swine Fever Viruses," Adenoviridae, Caulimoviridae, Myoviridae, Phycodnaviridae, Tectiviridae, Papovaviridae, Circoviridae, Parvoviridae, Hepadnaviridae, Cystoviridae, Birnaviridae, Reoviridae, Coronaviridae, Flaviviridae, Togaviridae, "Arterivirus," Astroviridae, Caliciviridae, Picornaviridae, Potyviridae, Retroviridae, Orthomyxoviridae, Filoviridae, Paramyxoviridae, Rhabdoviridae, Arenaviridae, and Bunyaviridae.

In one embodiment, the virus is herpes, pox, papilloma, corona, influenza, hepatitis, sendai, sindbis and vaccinia viruses, west nile, hanta, and viruses which cause the common cold.

In yet another embodiment, contacting a fungus with the composition of the invention inactivates the fungus. In one embodiment, the fungus is a yeast, such as, for example various species of *Candida* (e.g., *Candida albicans*) or filamentous yeast including but not limited to *Aspergillus* species or dermatophytes such as *Trichophyton ubrura, Trichophyton mentagrophytes, Microsporum canis, Microsporum gypseux,* and *Epiderophytonfloccosum*, and types thereof, as well as others.

The composition of the invention can also be used for mold remediation for building, equipment, and facilities. Examples of molds include, but are not limited to *Cladosporium, Fusarium, Alternaria, Curvularia, Aspergillus,* and *Penicillium*.

The disinfectant described herein can also be used as an aerosol or spray to eliminate odors, e.g. as a room or fabric deodorizer.

In one embodiment, the disinfectant described herein is used as a mouthwash to eliminate bad breath and to reduce the presence of oral microorganisms. Although not necessary, additional conventional components may be added to the disinfectant of the invention as in mouthwashes of the prior art. For example, softeners such as glycerin may be added to enhance the lubricous mouth feel of the mouthwash as it is used and to provide a refreshing, moist, organoleptic feeling thereafter. Glycerin may be incorporated in amounts of from about 0.05% w/v to about 10.0% w/v, and preferably in an amount of about 7.5% w/v. Sweeteners such as aspartame or sodium saccharin and the like may be added for better taste in amounts of from about 0.005% w/v to about 1.0% w/v, and preferably in an amount of approximately 0.05% w/v. Other essential oils can be added to alter the flavor. Zinc chloride or other zinc salts e.g. zinc gluconate, zinc sulfate etc., may be added as an astringent for an "antiseptic cleaning" feeling in an amount of from about 0.0025% w/v to about 0.200% w/v.

In one embodiment, the disinfectant described herein is used in medical applications, such as to clean skin wounds, or skin surfaces. The disinfectant can also be used as a hand sanitizer. The disinfectant is very potent and highly effective at killing microorganisms including, but not limited, to *Salmonella cholerasuis, Staphylococcus aureaus, Pseudomonas aeruginosa, Escherichia coli, Streptococcus pneumonia, Listeria monocytogenes* and *influenza*.

In one embodiment, the disinfectant described herein is used as germicidal for disinfecting/cleaning foodstuff or plant matter. Hydrogen peroxide solutions have also been found to be effective at inhibiting sprouting and rooting of foodstuffs, such as potatoes or other vegetables, thereby extending the shelf life of perishable food stuffs and plant matter. See for example, U.S. Pat. No. 6,348,187 which is herein incorporated by reference. The disinfectant composition can be sprayed directly on plant matter or mixed with soil to discourage infestation with parasitic organisms.

In one embodiment, the composition is used in the food industry in preventing and treating food contaminated with pathogens. Thus, such compositions may be used to reduce or inhibit microbial growth or otherwise abrogate the deleterious effects of microbial contamination of food. For example, the composition can be used to kill bacteria and fungus on poultry eggs, fruit, vegetables, and meat. Also, the inclusion of the compositions of the invention within the food product itself would be effective in killing bacteria that may have been accidentally contaminated meat or poultry. The composition can be included in juice products to prevent growth of certain fungi, which cause contamination and lead to production of mycotoxins. For these applications, the compositions is applied in food industry acceptable forms such as washes, dips, additives, preservatives, or seasonings. The use of media and agents for additives, preservatives, and seasonings that are acceptable in food industry is well known in the art. Except insofar as any conventional additives, preservatives and seasonings are incompatible with the disinfectant composition of the invention, their use in preventing or treating food born microbes and their toxic products is contemplated. Supplementary active ingredients may also be incorporated into the compositions.

In one embodiment the disinfectant is loaded onto a cleaning wipe. The cleaning wipe, upon which the disinfectant composition is loaded thereon, is made of an absorbent/adsorbent material. Typically, the cleaning wipe has at least one layer of nonwoven material. Nonlimiting examples of commercially available cleaning wipes that can be used include DuPont 8838, Dexter ZA, Dexter 10180, Dexter M10201, Dexter 8589, Ft. James 836, and Concert STD60LN, and Ahlstrom 4759. All of these cleaning wipes include a blend of polyester and wood pulp. Dexter M10201 also includes rayon, a wood pulp derivative. The loading ratio of the cleaning composition onto the cleaning wipe is about 2-5:1, and typically about 3-4:1. The disinfectant composition is loaded onto the cleaning wipe in any number of manufacturing methods. Typically, the cleaning wipe is soaked in the disinfectant composition for a period of time until the desired amount of loading is achieved.

In one embodiment, the disinfectant composition is packaged in a pressurized gas aerosol can. Common aerosol propellants include butane, isobutane, liquefied natural gas, and propane.

The invention provides methods for disinfecting surfaces to inactivate pathogenic organisms comprising contacting a surface with the disinfectant composition of the invention. The step of contacting can involve contacting any substrate, which may be or is suspected to be contaminated, with the composition of the invention. By substrate it is meant, without limitation any subject, such as a human or an animal (contact can be in vivo or ex vivo, any article, any surface, or any enclosure. A pathogenic microorganism can be, without limitation, a bacteria, a virus, a fungus, a protozoan or a combination thereof.

The step of contacting can be performed for any amount of time sufficient to inactivate a microorganism. In one embodiment, inactivation occurs within about 5 minutes to about 10 minutes after initial contact. However, it is understood that when the emulsions are used in a therapeutic context and applied topically or systemically, the inactivation may occur over a longer period of time, for example, 5,10, 15,20, 25 30,60 minutes or longer after administration.

The step of contacting can be performed using any appropriate means of application. For example, compositions can be administered by spraying, fogging, misting, exposure to aerosols, wiping with a wet or saturated cloth or towlette, drenching, immersing.

The invention further provides a method for reducing the number of mold spores on a surface. The method comprises contacting the mold spores with the composition comprising hydrogen peroxide ($H_2O_2$), orange terpene oil, orange valencia oil, a non-ionic emulsifier (e.g. polysorbate 80), and distilled or deionized water ($H_2O$). Any mold can be treated using methods of the invention.

EXAMPLES

Example I

Efficacy

Methods

The germicidal spray composition comprising 60% distilled water, 10% polysorbate 80, 5% orange valencia oil, 10% orange terpene oil, and 15% of a 35% Hydrogen peroxide solution was tested for its ability to kill *Salmonella cholerasuis, Staphylococcus aureaus, Pseudomonas aeruginosa, Escherichia coli, Streptococcus pneumonia*, and *Listeria monocytogenes*. Three lots were tested, one being at least greater than 60 days old.

The analysis was performed per "Germicidal Spray Test", AOAC $17^{th}$ edition, 6.3.03, versus *Salmonella cholerasuis* ATCC 10708, *Staphylococcus aureaus* ATCC 6538, *Pseudomonas aeruginosa* ATCC 15442, *Escherichia coli* ATCC 8739, *Streptococcus pneumonia* ATCC 49619, and *Listeria monocytogenes* ATCC 19113. Testing was performed as required by the EPA FIFRA. The AOAC procedure used in this study is a widely known and accepted method for disinfectant evaluation.

Microorganisms were grown for 48 h in nutrient broth. Glass slides were then inoculated with the grown culture and the inoculated slides were subsequently exposed to the germicidal spray for 10 minutes (60 microorganism inoculated slides/lot/microorganism were tested). After exposure to the disinfectant, slides were used as inoculates in leethen media and microorganism growth determined. Positive, negative and inhibition controls were performed.

Results

All organisms tested were found to be susceptible to the disinfectant. Absolutely no growth was observed in media that was inoculated with the organism slides which were exposed to disinfectant. Controls included uninoculated containers of leethen broth (media controls) and sterile uninoculated glass slides (negative control), there was no growth; Glass slides inoculated with organism and a sterile glass slide immersed in test disinfectant (inhibition control), there was no growth which indicates that the letheen broth neutralizes the disinfectant; Glass slide inoculated with organism (viability control), there was growth; and Glass slide inoculated with organism (enumerated), >$10^6$ cfu.

Example II

EPA Acute Oral Toxicity

Methods

The germicidal spray composition comprising 60% distilled water, 10% polysorbate 80, 5% orange valencia oil, 10% orange terpene oil, and 15% of a 35% Hydrogen peroxide was tested for toxicity according to protocol number X5D050G, which incorporates by reference Northview Standard Operating Procedure 16D-05 and is on file in Northview Pacific Laboratories, Inc. No amendments were made to the protocol.

A limit screen test was performed using three female Sprague-Dawley rats, which received an oral limit Dose of 50000 mg/kg of the test article. The animals were observed for mortality, weight change and toxic signs for a two week period. Animals were observed daily and weighed on days 7 and 14.

Animal preparation. The animals were fasted overnight before dose administration. During fasting they continued to receive water ad libitum. Food was withheld until four hours after dosing in order to facilitate gastrointestinal absorption of the test article.

Sample preparation. The density of the test article was 1 g/ml and shaken before use.

Dosing procedure. The dose was administered by means of a gavage needle attached to a hypodermic syringe. The test animals received a 5 mL/kg solution containing the test article. Three rats were dosed on the first day of dosing. Because all three rats survived no further testing was required.

Results

A single oral administration of germicidal spry product at a limit dose of 5000 mg/kg produced no mortalities. The clinical observations are summarized in FIG. 1. All animals gained weight during the test period and no abnormalities upon necropsy were observed.

Example III

EPA Primary Eye Irritation Test

Method

The germicidal spray composition comprising 60% distilled water, 10% polysorbate 80, 5% orange valencia oil, 10% orange terpene oil, and 15% of a 35% Hydrogen peroxide was tested for toxicity according to protocol number X5D051G, which incorporates by reference Northview Standard Operating Procedure 16D-08 and is on file in Northview Pacific Laboratories, Inc. No amendments were made to the protocol.

Six New Zeland Rabbits were used. On the day prior to dosing the rabbits eyes were examined using fluorescein sodium opthamalic strips and ultraviolet light. Only rabbits without eye defects or irritation were used. A 100 ul volume of test material was introduced into the conjuctival sac of the right eye of each rabbit. The left eye remained untreated. The treated eye was washed out with physiological saline 24 hours after dosing.

The eyes were examined and graded for ocular reaction at 1, 24, 48, and 72 hours after application of the test substance for corneal ulceration or opacity, inflammation of the iris, or redness and chemosis of the conjunctivae. The results are interpreted according to the Kay and Calandra Method (Kay J. H. & Calandra, J. C., "Interpretation of eye irritation tests", Journal of society of cosmetic chemists, 13:281-289, 1962).

Results

Based on the Kay and Calandra method of classifying eye irritation properties, the test article was determined to be moderately irritating to eyes of New Zeland Rabbits.

All animals remained healthy throughout the study period. The primary eye irritation scores are shown in FIG. 2. A table indicating the scale for scoring the ocular lesions can be found in FIG. 3. There was significant irritation in all 3 animals beginning at the 1 hour scoring and continuing through the 96 hour scoring. The scores all went back to "0", normal scoring, by the 7-day scoring.

Example IV

EPA Primary Dermal Irritation Test

Method

The germicidal spray composition comprising 60% distilled water, 10% polysorbate 80, 5% orange valencia oil, 10% orange terpene oil, and 15% of a 35% Hydrogen peroxide was tested for toxicity according to protocol number X5D052G, which incorporates by reference Northview Standard Operating Procedure 16D-07 and is on file in Northview Pacific Laboratories, Inc. No amendments were made to the protocol.

Three New Zealand White rabbits were used. One day prior to dosing, the hair on each animal's back was removed with clippers. A one inch square gauze patch containing a 0.5 mL volume of the test article was applied to the shaved skin on each animal. The patch was held in place with surgical tape. After application the trunk of each animal was wrapped with gauze to prevent the animal from disturbing the test patch. During an exposure period of 4 hours, the animal was not restrained in any way. After the exposure period, the patch was removed and test article residues were gently rinsed off with a non-irritating solvent, water. The dosing sites were re-examined and scored 30-60 minutes, 24, 48, and 72 hours after unwrapping. Additional scores were recorded 7 and 14 days after unwrapping to determine the time course of resolution for any irritation that persisted.

The animals were observed for mortality, signs of ill health, or reaction to treatment.

Results

Signs of edema, erythema, and or eschar formation were scored for each animal according to the criteria in FIG. 4. The individual scores for edema and erythema are shown in FIG. 5. On the day of patch removal, all three animals exhibited slight erythema (score of 1) at the 30-60 minute scoring and one animal (38383) had slight erythema to the 48 hour scoring. There were no irritation responses observed at the 72 hour observation for any of the animals. All animals remained healthy throughout the study period. The test article was slightly irritating to the skin of three test animals.

Example V

Virucidal Efficacy of the Composition of the Invention

Method

The germicidal spray composition comprising 60% distilled water, 10% polysorbate 80, 5% orange valencia oil, 10% orange terpene oil, and 15% of a 35% Hydrogen peroxide was tested for virucidal efficacy. MICROBIOTEST INC. (the microbiology and virology laboratory 105 Carpenter Drive, Sterling, Va. 20164) performed the tests from Feb. 10, 2005 to Feb. 18, 2005 and all raw data, protocol, protocol modifications, test material records, and the final report, are stored in the archives at MICROBIOTEST INC. (105 Carpenter Drive, Sterling, Va. 20164) or at a controlled facility offsite. The Virucidal Efficacy test was performed as detailed in the following protocol from MICROBIOTEST INC.:

Protocol for Virucidal Efficacy Test

Test conditions: Challenge virus: Avian Influenza A virus, Turkey/W is/66 strain (H9N2), Charles River Laboratories; Host: Embryonated chicken eggs, B&E Eggs; Active ingredient in test product: Hydrogen peroxide; Neutralizer used: Earle's Balanced Salt Solution containing 0.3% Thioglycolic acid and 0.1% Catalase; Contact time: 10 minutes; Contact temperature: Ambient room temperature (22° C.); Dilution: Ready to use as received; Media and reagents: Earle's Balanced Salt Solution, Earle's Balanced Salt Solution containing 0.3% Thioglycolic acid and 0.1% Catalase, Sephacryl S-1000, Chicken red blood cells, Phosphate Buffered Saline containing 0.5% fetal bovine serum, Phosphate Buffered Saline Objective: The test is designed to substantiate virucidal effectiveness claims for a product to be labeled as a virucide. It determines the potential of the test agent to disinfect hard surfaces contaminated with viruses. The test is designed to stimulate consumer use and conforms to EPA Guidelines DIS/.TSS-7, November 1981, and follows the procedure outlined in the American Society for Test Materials (ASTM) test method designated E 1053-97.

Testing conditions: Virus will be dried on a sterile glass Petri dish at ambient temperature. Test agents specified by the sponsor in the miscellaneous section of the protocol will be used to treat the dried virus according to the label claims. After a defined exposure period, the neutralized test agent-virus mixture will be scraped from the surface, neutralized and assayed for the presence of infectious virus.

Materials: Test, control and reference substances will be supplied by the sponsor of the study. The test agent will be tested as supplied by the sponsor unless directed otherwise. All operations performed on the test agent such as dilution or specialized storage conditions must be specified by the sponsor before initiation of testing. The sponsor assures MICROBIOTEST testing facility management that the test agent has been appropriately tested for identity, strength, purity, stability, and uniformity as applicable. MICROBIOTEST will retain all unused test agents for a period of at least three months after completion of the test, then return them to the sponsor of the study or discard them in a manner that meets the approval of the safety officer.

Materials supplied by MICROBIOTEST, including, but not limited to: 1) Challenge virus (requested by the sponsor of the study): Avian Influenza virus. 2) Host: Embryonated chicken eggs. 3) Laboratory equipment and supplies. 4) Media and reagents: Media and reagents relevant to the virus-host system and test agent being tested will be documented in the first project sheet and/or the data pack.

Test system identification: All Petri dishes, dilution tube racks, and host-containing apparatus will be labeled with virus identification and project number.

Experimental design: Procedures involved in performance of virucidal studies are described a series of SOPs and logs that are maintained at MICROBIOTEST. The procedures used in different phases of the study will be documented in the data pack.

Inoculum preparation: Viral stocks are purchased from reputable sources that identify them by scientifically accepted methods and are propagated at MICROBIOTEST. Records are maintained that demonstrate the origin of the virus. The virus stocks are stored at an ultra-low temperature. Frozen viral stocks will be thawed on the day of the test (fresh stock cultures may be used at the discretion of the Study Director).

Carrier preparation: An aliquot of 0.2 mL of stock virus will be spread, with a cell scraper, over an area of approximately 4 in$^2$ that has been marked on the underside of pre-sterilized Petri dishes. The virus will be allowed to dry for 30 to 60 minutes at room temperature. The drying time and temperature will be recorded. One carrier will be prepared for each test agent and the plate recovery control. One plate will be prepared for the neutralizer effectiveness control using an appropriate medium.

Test agent preparation: The agent will be prepared according to the sponsor's directions or proposed label claims.

Test: After the carrier(s) are properly prepared, 2.0 mL of the test agent will be added. The plates will remain at the temperature and for the time specified by the sponsor. Following the contact period, the test agent will be neutralized with 2.0 mL of the appropriate neutralizing solution and the mixture will be scraped from the surface of the dish with a cell scraper. This will be considered approximately a one $\log_{10}$ dilution. If columns are used, each sample will be loaded into separate pre-spun Sephacryl columns. Following passage through columns, the eluate will be removed aseptically and serially diluted. If columns are not used, serial dilutions of neutralized virus-test agent mixture will be prepared in using an appropriate diluent. For spray type agents, the agent will be used as the sponsor directs, the volume dispensed will be measured and an equal volume of neutralizer will be used. Following the contact time, the procedure for processing the samples will be the same as described earlier.

Viral host culture: Two-tenths mL of selected dilutions of the neutralized inoculum/disinfectant mixture will be inoculated intra-allantoically in embryonic eggs and incubated for 5-7 days at 37±2C. Four determinations will be recorded for each dilution of both tests and controls. The eggs will be candled one-day post-inoculation of test and control samples. All dead embryos will be discarded and the data will be recorded. Following completion of the incubation period, the eggs will be candled and then kept at 2±2C overnight. Afterwards, the allantoic fluid will be harvested and kept at 2±2C until assay. The samples will be assayed for the presence of replicating virus using hemagglutination assay following SOP 1006.11 (current version) and the results will be recorded.

Controls

Neutralizer effectiveness (NE): This control will determine if residual active ingredient is present after neutralization. One lot of the test agent will be used for the neutralizer effectiveness control. This control will be processed exactly as the test procedure but instead of viral inoculum, appropriate media will be added. Post neutralization, a 1.0-mL sample will be divided into three portions, using two for toxicity-related controls and the other for neutralizer effectiveness. A 0.5 mL sample will be serially diluted, after which 100 µL of diluted virus will be added to each dilution and held for a period greater than or equal to the contact time. Then these samples will be used to inoculate host embryos as described for the test procedure.

Toxicity (TX): The toxicity sample, acquired from the neutralizer effectiveness control, will be diluted and have no virus added. Selected dilutions will be inoculated into the host and incubated in the same manner as the rest of the test and control samples. These effects are distinct from virus-specific cytopathic effects, which will be evident in the stock titer and plate recovery control cultures.

Toxicity-related viral interference control: The test agent may not be effective against the challenge virus yet be toxic to the host employed to detect its infectivity and may inhibit accurate interpretation of the test. To determine the possibility of such interference by residual toxic molecules, host treated with serially diluted neutralized test agent will be infected with a known number of infectious virions. Post-incubation they will be scored and compared with non-treated infected host cells control. This will rule out any possibility of toxicity-related viral interference remaining in the neutralized test agent post-contact time.

Plate recovery (PRC): The carrier used will be prepared as the test. A volume of an appropriate media equivalent to that of the test agent will be added to the dried virus. Post contact time this sample will be treated as the test. This control will determine the relative loss in virus infectivity resulting from drying and neutralization alone. The results from this control will be compared with the test results to confirm recovery of at least four $\log_{10}$ of infectious virus following drying and neutralization. This titer will be compared with the titers of the test results to reach the acceptable test criteria. When samples are required to pass through the Sephacryl columns, a column titer control (CTC) will be performed by assaying a portion of PRC before passing through the columns to determine the effect on infectious virus titer after passage through the columns.

Column titer control (CTC): This control will be performed to determine any effects the columns may have on infectious virus titer. It will only be performed if columns are used in the study. The sample for this control will be acquired from a portion of the PRC, prior to passing through the columns, and will be serially diluted in an appropriate media. It will then be processed in the same manner as the test.

Virus stock titer (VST): In order to verify the virus stock titer, al aliquot of the virus inoculum will be serially diluted in an appropriate media and processed, as well as assayed as described for the test.

(HVC) Eggs For Clarification: Four eggs will be inoculated with an appropriate media during the incubation phase of the study. This control will demonstrate that cells remain viable throughout the course of the assay period. In addition, it will confirm the sterility of the media employed throughout the assay period.

Calculation: The 50% embryo infectious/lethal dose per mL (EID/ELD$_{50}$/mL) will be determined using the method of Reed and Muench, Am. J. of Hyg. 1938, 27:493. The test results will be reported as the reduction of the virus titer due to treatment with test agent expressed as $\log_{10}$.

Product evaluation criteria: According to the regulatory agencies, the test agent passes the test if there is complete inactivation of the virus at all dilutions. When toxicity is evident, at least a three-log reduction in titer must be demonstrated beyond the toxic level. Test acceptance criteria: The test will be acceptable for evaluation of the test results if the criteria listed below are satisfied. The study director may consider other causes that may affect test reliability and acceptance, a) The infectious virus recovered from the PRC control must be $\geq 4-\log_{10}$. b) Viral-induced toxicity must be distinguishable from test agent induced toxic effects.

Results

Results are presented in FIGS. 6-7. Avian Influenza virus was exposed to the germicidal spray composition for 10 minutes at ambient room temperature (22° C.). The germicidal spray inactivated Avian Influenza virus (FIG. 6), as no virus was detected after exposure. All controls met the criteria for a valid test (FIG. 7*a-c*). Virus was not recovered in the host viability control (FIG. 7*c*) confirming media sterility and host viability.

Example VI

Inhibition of Methicillin Resistant Strain of *Staphylococcus aureus* (MRSA)

Methods

The germicidal spray composition comprising 60% distilled water, 10% polysorbate 80, 5% orange valencia oil, 10% orange terpene oil, and 15% of a 35% Hydrogen peroxide (Citroxin) was tested against the Methicillin resistant strain of *Staphylococcus aureus* ATCC #33591 (MRSA) in a microbial inhibition study.

The microbial inhibition study is commonly used to determine antimicrobial effectiveness of antibiotics against know pathogens in a clinical microbiological setting. In this study three concentrations of each product (1×, 0.5×, 0.1×) were evaluated. A suspension of the MRSA strain was prepared in sterile phosphate buffer solution to a turbidity of 3 McFarland to achieve robust cell concentration and homogeneity. 1.0 mL of the suspension was placed onto a Petri dish dedicated for each sample submitted.

The liquid was distributed evenly across each Petri dish and the excess liquid removed for the purpose of creating a lawn growth of bacteria throughout the plate. The plates were placed into a 35° C. incubator, inverted and allowed to dry for 10 minutes. Following this, each plate was inoculated with three concentrations of the respective samples being studied. The inoculated plates were incubated for 24 hours and evaluated for inhibitory growth. Determination of inhibition is made by a zone of clearing around the inoculated area on the plate where each concentration of sample was placed. Pictographs of each test follow the summary chart below.

Determination of inhibition (were applicable) is based on the distance in millimeters where the bacteria can not grow in proximity to each sample concentration. The distance is reported in millimeters of radius from the foci point of sample inoculation. The diameter of the zone of clearing is measured and the diameter of the liquid antimicrobial sample for each concentration is subtracted. The resulting number is divided by 2 to give a radius of inhibition from the inoculation point.

Results

The table 1 below shows that the radius of inhibition from the inoculation point of MRSA was 13.0 mm, 11.5 mm, and 6.5 mm for 1×, 0.5× and 0.1× concentrations of Citroxin, respectively. Accordingly, the germicidal spray composition comprising 60% distilled water, 10% polysorbate 80, 5% orange valencia oil, 10% orange terpene oil, and 15% of a 35% Hydrogen peroxide is a potent inhibitor of MRSA growth. Control plates showed no inhibition of growth.

TABLE 1

| Sample | Sample Concentration | 24 Hr Inhibition results (radius in millimeters, mm) |
| --- | --- | --- |
| Citroxin lot#100207 | 1X | 13.0 mm |
|  | 0.5X | 11.5 mm |
|  | 0.1X | 6.5 mm |

All references described herein are incorporated herein by reference.

The invention claimed is:

1. A method of inhibiting growth of a microorganism comprising contacting said microorganism with a composition comprising hydrogen peroxide ($H_2O_2$) orange terpene oil, orange valencia oil, a non-ionic emulsifier, and distilled or deionized water ($H_2O$).

2. The method of claim 1, wherein the orange terpene oil is present in the composition from 5% to 40% v/v, the orange valencia oil is present in the composition from 5% to 40% v/v, the non-ionic emulsifier is present in the composition from 5% to 50% v/v, the distilled or deionized $H_2O$ is present in the composition from 5% to 80% v/v and the hydrogen peroxide is present in the composition from 1.5% to 8% w/v $H_2O_2$.

3. The method of claim 1, wherein the non-ionic emulsifier present in the composition is polysorbate 80.

4. The method of claim 1, wherein the composition comprises 5.25% w/v $H_2O_2$, 10% v/v orange terpene oil, 5% v/v orange valencia oil, 10% v/v polysorbate 80, and 60% v/v distilled water.

5. The method of claim 1, wherein the composition further comprises oil of rosemary.

6. The method of claim 1, wherein the composition further comprises an antimicrobial agent.

7. The method of claim 1, wherein the composition further comprises a surfactant.

8. The method of claim 1, wherein the composition is formulated as a gel, a spray, a paste, a foam, or a disinfecting wipe.

9. The method of claim 1, wherein the microorganism is a bacteria, a fungus, or a mold spore.

10. The method of claim 9, wherein the microorganism is a bacteria selected from the group consisting of *Salmonella cholerasuis, Staphylococcus aureaus, Pseudomonas aeruginosa, Escherichia coli, Streptococcus pneumonia,* and *Listeria monocytogenes.*

11. The method of claim 10, wherein the microorganism is *Staphylococcus aureus* that is Methicillin resistant (MRSA).

\* \* \* \* \*